US005279286A

United States Patent [19]

Chen

[11] Patent Number: 5,279,286

[45] Date of Patent: Jan. 18, 1994

[54] MASK

[76] Inventor: Kwang-Ho Chen, No. 407, Sec. 6, Chung Hsiao E. Rd., Taipei, Taiwan

[21] Appl. No.: 921,241

[22] Filed: Jul. 29, 1992

[51] Int. Cl.[5] .......... A61M 15/00

[52] U.S. Cl. .......... 128/201.19; 128/201.24; 128/206.23

[58] Field of Search .......... 128/202.27, 206.17, 128/206.23, 206.24, 201.19, 201.24, 201.25, 202.11

[56] References Cited

U.S. PATENT DOCUMENTS

| | | | |
|---|---|---|---|
| 2,238,492 | 4/1941 | Leguillon | 128/206.23 |
| 2,420,281 | 5/1947 | Zbar | 128/206.23 |
| 2,597,764 | 5/1952 | Tucker et al. | 128/201.24 |
| 2,814,293 | 11/1957 | Gabb et al. | 128/201.19 |
| 2,996,722 | 8/1961 | Jacobs | 128/206.23 |
| 3,259,127 | 7/1966 | Klinger et al. | 128/206.23 |
| 3,314,424 | 4/1967 | Berman | 128/201.19 |
| 3,315,673 | 4/1967 | Morton, Jr. | 128/206.23 |
| 3,968,793 | 7/1976 | Geissler | 128/206.23 |
| 4,164,942 | 8/1979 | Beard et al. | 128/201.19 |
| 4,875,477 | 10/1989 | Waschke et al. | 128/206.24 |

*Primary Examiner*—Edgar S. Burr
*Assistant Examiner*—Aaron J. Lewis
*Attorney, Agent, or Firm*—Morton J. Rosenberg; David I. Klein

[57] ABSTRACT

A mask having a removable respirator, a viewing glass and flexible fastening straps on the rear side thereof is provided. The respirator and the viewing glass are fixed by respective fixing rings to suitable positions in front of the mask. The fixing rings are tightened by a screw having a turning grip formed on the top thereof, so that it makes possible simple disassembly without the use of tools. The screw is also provided with a flange adapted for convenient attachment of a speech microphone thereto.

1 Claim, 2 Drawing Sheets

MASK

BACKGROUND OF THE INVENTION

The present invention relates to a mask of a novel design, more specifically it relates to such a design of mask which permits the respirator and the viewing glass, both being components thereof, to be simply and promptly removed, without recourse to any other tools, so as to facilitate cleanup services. Further, it permits ready and reliable attachment of a speech microphone to a given side thereof, thus achieving its novelty and advantageous features.

Conventionally, various models of masks, either for anti-gas, or for anti-smoke purposes, owe their structure to the mounting of the respirator and of the viewing glass to the front-piece, by such fixing parts as the frame, screws and nuts. The front-piece being complete with fastening straps.

With models of such conventional design, apart from the necessity for a secured interconnection between the respirator and the viewing glass, consideration must also be given to the interfacing anti-leak requirements, so in the assembling process tools are indispensable, like a screwdriver and similar items, to lock the respirator, viewing glass and the front-piece in a tightly sealed state. Similarly, the same tooling is needed when the user wants to remove these components to undertake cleanup or maintenance services, such service being preconditioned by unscrewing, and disassembling efforts.

Disassembling a mask by means of necessary tools, in the exercise of regular servicing procedures, is quite all right. It can indeed prove a very big problem under unexpected situations, for instance in pre-mission examinations, when a poor seal is identified in the wake of permeating smoke at the scene of a fire, or when the frame loosens so as to leak, due to collisions. All of these situations prescribe that a suitable and workable tooling be readily available.

All of the aforementioned drawbacks and inconveniences can only be eliminated, and the efficiency of conventional masks enhanced, by the design of a device which permits easy adjustment of the locking means, assembling, and disassembling of the mask proper, just as does certain models of pistols which can be readily disassembled without any tooling for facilitating cleanup services. However, such a design has heretofore not been available.

SUMMARY OF THE INVENTION

So in view of the foregoing reasoning the present invention is introduced in the form of a novelly designed anti-gas mask. In particular, the invention is directed to the provision of a mask which permits easy assembly and disassembly of the respirator and of the viewing glass, both structurally integral therewith. The present invention facilitates convenient cleanup and servicing operations, by this feature, far exceeding existing models of masks anywhere.

Stated in other words, the main characteristic feature of the present invention lies in the presentation of such an anti-gas mask which permits easy lock adjustment, assembly and disassembly of the respirator and of the viewing glass, anytime and anywhere. The user can therefore promptly adjust the mask to the safest working condition under whatever circumstances arise and in any emergency.

Still another characteristic feature of the present invention is the provision of an anti-gas mask which permits the attachment of a speech microphone to the front-piece for communication without ad hoc provision of a microphone jack thereon.

DETAILED DESCRIPTION OF THE DRAWINGS

Other features and advantages of the invention can be better appreciated as the disclosure proceeds with reference to the accompanying drawings in which.

DETAILED DESCRIPTION OF THE PREFERRED EMBODIMENT

Figure 1:
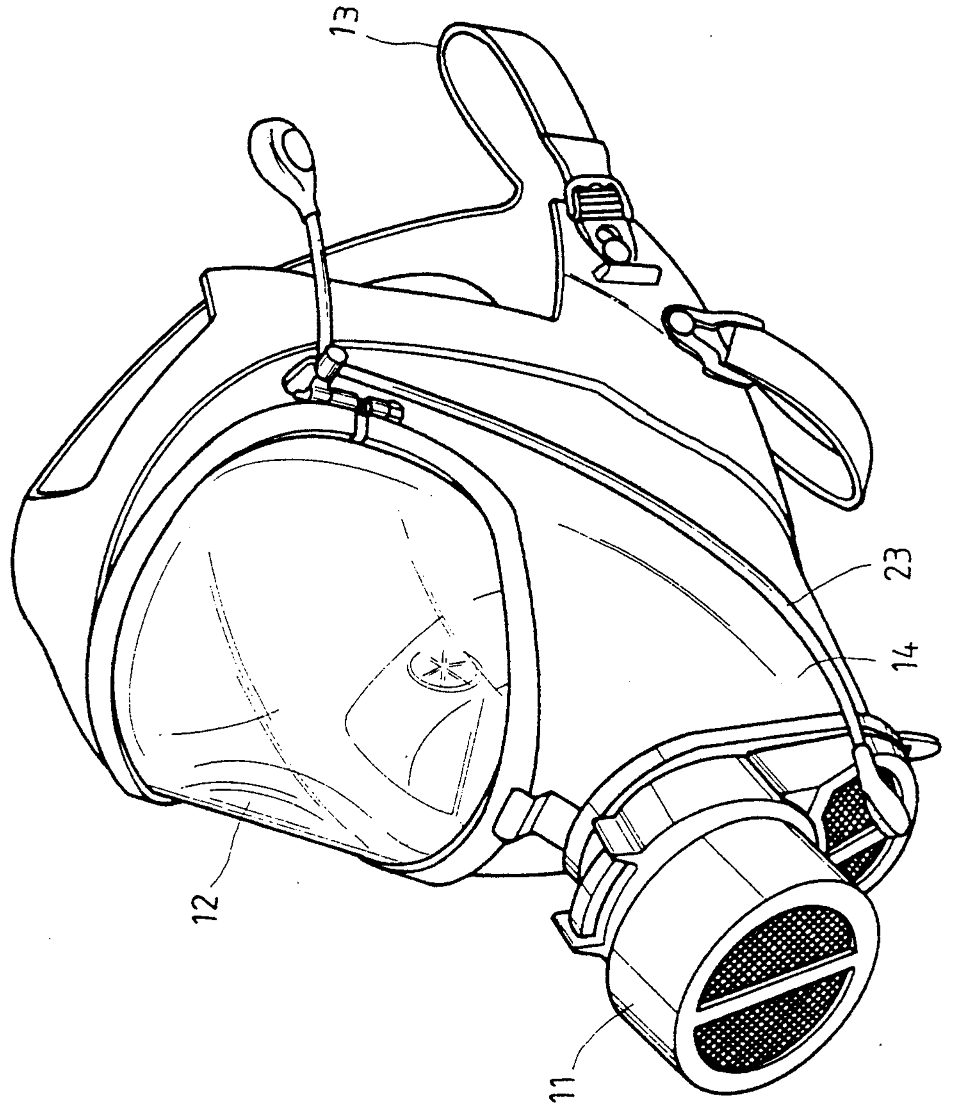
FIG. 1 is a perspective view of the inventive mask.

Referring to FIG. 1, it will be seen that the inventive mask consists essentially of the respirator 11, viewing glass 12, facial covering 14 complete with flexible rear strap 13, set in a framework permitting easy assembly and disassembly of them all.

Figure 2:
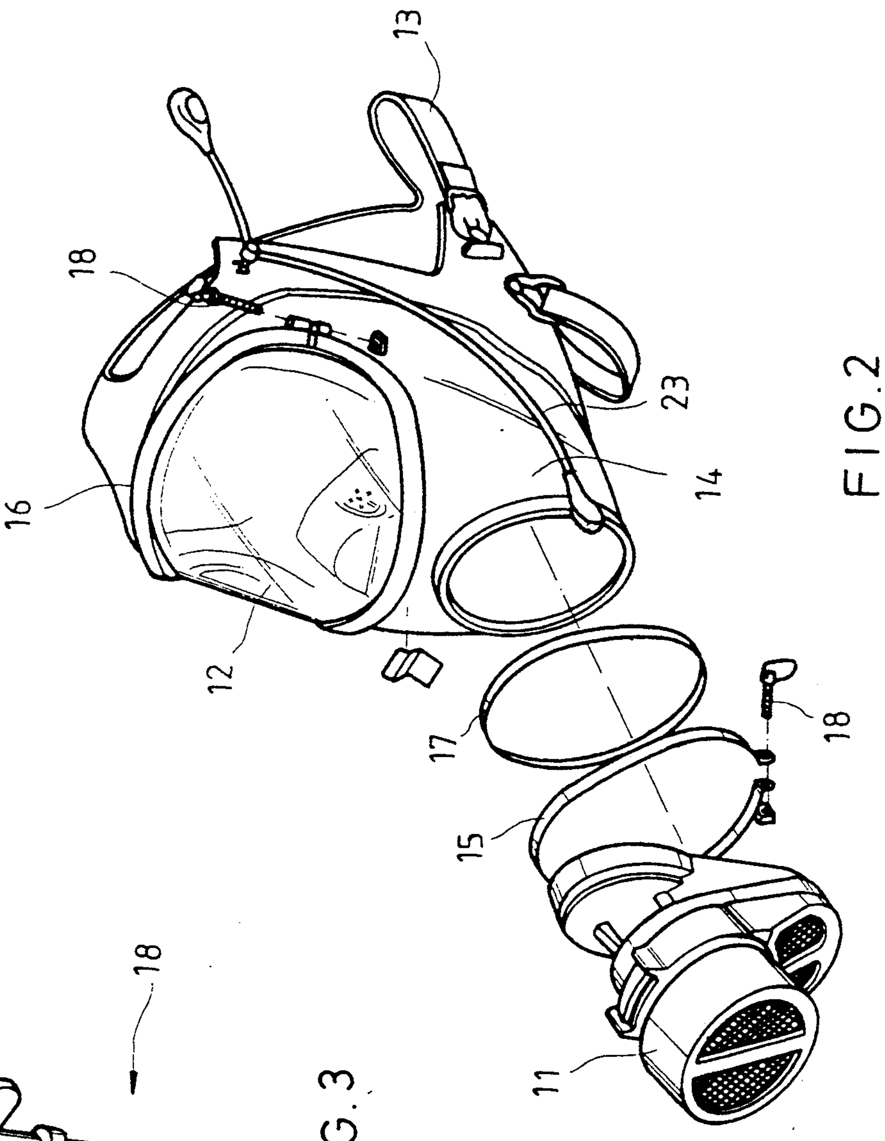
FIG. 2 is an exploded perspective view of the inventive mask.

Referring to FIG. 2, it will be seen that the facial covering 14 accommodates two fixing rings 15 and 16, each serving to hold in position the respirator 11, and the viewing glass 12, respectively. On the upper side of each fixing ring 15, 16 is provided a compression means 17 which serves to tighten up the seal against leakage. Illustration of such being made for the respirator 11 only, as the structural layout of the viewing glass 12 is the same, and is thus omitted on the drawing. Both of the fixing rings or hoops 15 and 16 are locked by a screw 18 having a movable stem 22 on top, so that both the respirator 11 and the viewing glass 12 can be brought tight in association with the facial covering 14.

Figure 3:
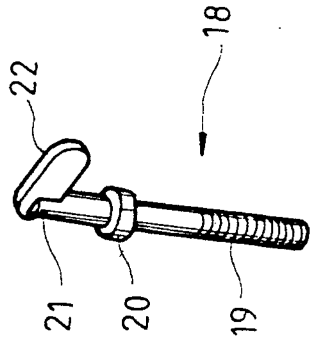
FIG. 3 is an illustration of the screw serving to lock the framework of the invention.

As illustrated in FIG. 3, the screw 18, used to clamp the fixing hoops, is composed characteristically of threads 19, a stop flange 20, with the upper portion formed into a pin 21 accommodating a turning grip 22, in the upwardly arranged layout. To lock a hoop 15, 16 into position using this screw 18, force is applied to the turning grip 22 on the top thereof, without having to prepare any other tool for the purpose. The respirator 11 and the viewing glass 12, are provided integral with the mask, but can be disassembled forthwith, thereby accommodating cleanup and maintenance services. Whenever there is slack felt in one of the hoops, the user may effect turning of screw 18 by means of grip 22, to secure the hoop in position, so that the mask in its entirety is maintained at optimum working status at all times.

The screw 18 that is formed with a stop flange 20, as previously discussed, has another additional function, that is, the user, a fire brigade member for instance, when entering a fire scene in answer to a call, may conveniently secure a speech microphone onto the stop flange 20. Thus, relieving the need to provide a microphone jack for holding the microphone somewhere on the mask.

I claim:

1. A mask securable to a user by a flexible strap and having a respirator and a viewing glass coupled thereto, comprising:

means for releasably coupling said respirator and said viewing glass to a frontal surface of said mask, said releasable coupling means including (1) a pair of fixing ring members, each of said pair of fixing ring members having a pair of opposing end portions, each of said pair of fixing ring members circumscribing a respective one of said respirator and said viewing glass for retention thereof to said mask frontal surface by affixing said opposing end portions one to the other, and (2) fastening means for reversible coupling of said fixing ring opposing end portions, said fastening means including:

a screw member having an externally threaded portion for reversible engagement with an internally threaded nut member;

a turning grip formed on an upper portion of said screw member, whereby said turning grip is used to rotate said screw member without use of a tool; and, a flange formed intermediate said threaded portion and said tuning grip; and, a microphone releasably coupled to said flange portion of a screw member.

* * * * *